United States Patent [19]

Fuchs et al.

[11] Patent Number: 4,853,477

[45] Date of Patent: Aug. 1, 1989

[54] SEPARATION OF DIASTEREOMERS OF CYCLOPROPANECARBOXYLIC ACID ESTERS

[75] Inventors: Rainer Fuchs; Wilhelm Stendel, both of Wuppertal, Fed. Rep. of Germany

[73] Assignee: Bayer Aktiengesellschaft, Leverkusen, Fed. Rep. of Germany

[21] Appl. No.: 87,574

[22] Filed: Aug. 20, 1987

[30] Foreign Application Priority Data

Aug. 29, 1986 [DE] Fed. Rep. of Germany ....... 3629387

[51] Int. Cl.$^4$ .......................................... C07C 69/612
[52] U.S. Cl. .................................. 558/398; 558/389; 558/388; 558/354
[58] Field of Search ............... 558/398, 389, 388, 354; 560/8, 55

[56] References Cited

U.S. PATENT DOCUMENTS

| | | | |
|---|---|---|---|
| 4,425,282 | 1/1984 | Jautelat | 558/398 |
| 4,463,014 | 7/1984 | Martel | 558/398 |

FOREIGN PATENT DOCUMENTS

| | | |
|---|---|---|
| 0537117 | 9/1980 | Australia . |
| 0564980 | 9/1980 | Australia . |
| 0046950 | 3/1982 | European Pat. Off. . |
| 2730515 | 1/1979 | Fed. Rep. of Germany . |
| 1604682 | 12/1981 | United Kingdom ............... 558/398 |

Primary Examiner—William R. Dixon, Jr.
Assistant Examiner—James M. Hunter
Attorney, Agent, or Firm—Sprung Horn Kramer & Woods

[57] ABSTRACT

A process for the separation of mutually diastereomeric forms of a cyclopropanecarboxylic acid ester of the formula

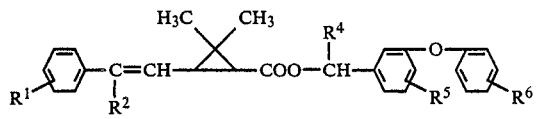

in which
$R^1$ represents hydrogen or halogen,
$R^2$ represents hydrogen or halogen,
$R^4$ represents hydrogen, Cn, —C≡CH or $CH_3$,
$R^5$ represents hydrogen or halogen, and
$R^6$ represents hydrogen or halogen, comprising reacting such ester in a first stage with about half or an equal molar amount of a second compound of the formula

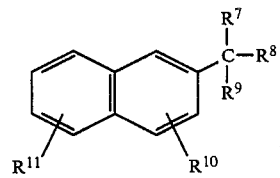

in which
$R^7$, $R^8$ and $R^9$ represent hydrogen or methyl, or, together with the C atom to which they are bound and with the adjacent C atoms of the basic structure form a fused 6-membered ring,
$R^{10}$ represents hydrogen, methyl, ethyl, halogen, amino, methylamino or dimethylamino, and
$R^{11}$ represents hydrogen, methyl or ethyl, to form complexes and in a second stage allowing the less soluble complex of one part of the diastereomers to crystallize out in the presence of a solvent selected from the group consisting of a lower aliphatic alcohol or aliphatic or cyclic hydrocarbon, and separating off the crystallized complex from the still dissolved material. The first stage complexes are new and the resulting purified enantiomeric mixture is also new.

13 Claims, No Drawings

SEPARATION OF DIASTEREOMERS OF CYCLOPROPANECARBOXYLIC ACID ESTERS

SUMMARY OF THE INVENTION

The present invention relates to a process for the separation of mutually diastereomeric forms of cyclopropanecarboxylic acid esters, new compounds which can be used for this, the preparation thereof, and a process for the purification of cyclopropanecarboxylic acid esters prepared industrially and of the acids on which they are based, and also a new pair of enantiomers of flumethrin.

Cyclopropanecarboxylic acids and the active compounds, prepared from them, of the class of the pyrethroids are produced, during their preparation, as mixtures of their optical and steric isomers. These isomers of the pyrethroids have different activities towards pests against whcih they are employed. The separation of, for example, the steric isomers is therefore of interest.

Pyrethroids are sensitive towards conventional physical purification methods, such as, for example, distillation. Their recrystallization often fails because they exist as oils, and because of their unfavorable dissolution behavior. On the other hand, the industrially prepared pyrethroids often contqain impuritied which must be removed before use of the active compounds. However, this purification is possible on an industrial scale only with considerable expense. It was therefore of interest to have available a process for the purification of pyrethroids which is simple and inexpensive to carry out, even on an industrial scale.

Pyrethroids of the following formula

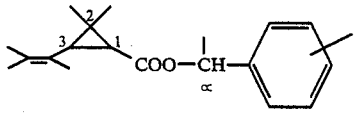

have centers of asymmetry on the C atoms 1, 3 and α They therefore exist in the from of the following isomers and the mixtures thereof:

| (a) | 1S | 3R | αS | (e) | 1S | 3S | αS |
| (b) | 1R | 3S | αR | (f) | 1R | 3R | αR |
| (c) | 1S | 3R | αR | (g) | 1S | 3S | αS |
| (d) | 1R | 3S | αS | (h) | 1R | 3R | αS |

The isomers (a) and (b), (c) and (d), (e) and (f) and (g) and (h) are mutually enantiomeric. All isomers which are not mutually enantiomeric are mutually diastereomeric.

The mutally enantiomeric forms represent mirror images of one another and differ only in the asymmetrical environment, for example by the rotation by their solutions of polarized light. They have no different chemical and physical properties through which they can be separated. Separation can only be accomplished using a chiral auxiliary reagent.

The mutually diastereomeric forms differ through the relative separation of the atoms to one another in the molecule. They therefore have different physical and chemical properties.

The individual isomers have different biological properties. It is therefore of interest to separate the active isomers from the less active isomers. Since the mutually enantiomeric isomers can only be separated using expensive chiral auxiliary reagents, it is sensible to separate the mutually diastereomeric isomers.

In principle, this separation is possible by distillation, recrystallization or chromatography. In the case of the pyrethroids, some of which are thermally sensitive, distillation is not possible, at least on an industrial scale. Separation by means of chromatography is also too complicated and expensive on an industrial scale. Recrystallization on an industrial scale often fails because the compounds are produced as oils or because it is difficult to find suitable solvent systems in which it may be carried out.

DETAILED DESCRIPTION

A process has been found for the separation of mutually diastereomeric forms of cyclopropanecarboxylic acid esters of the formula (I)

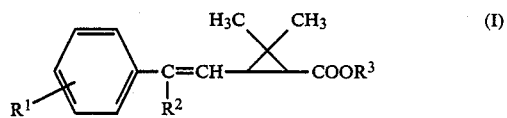

in which
$R^1$ represents hydrogen or halogen,
$R^2$ represents hydrogen or halogen, and
$R^3$ represents a radical of the formula (a)

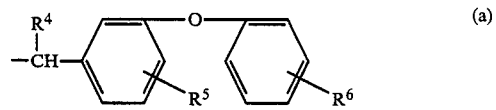

where
$R^4$ represents hydrogen, CN, —C≡CH or $CH_3$,
$R^5$ represents hydrogen or halogen, and
$R^6$ represents hydrogen or halogen,
which is characterized in that compounds of the formula (I), if appropriate in the presence of a diluent, are reacted in a first stage with compounds of the formula (II)

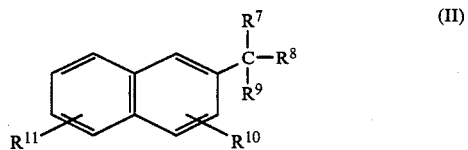

in which,
$R^7$, $R^8$ and $R^9$ represent hydrogen or methyl, or, together with the C atom to which they are bound and with the adjacent C atoms of the basic structure form a fused 6-membered ring.
$R^{10}$ represents hydrogen, methyl, ethyl, halogen, amino, methylamino or dimethylamino, and
$R^{11}$ represents hydrogen, methyl or ethyl to form a complex in the ratio of compounds I:II of 1:1 or 2:1 and, in a second stage, the less soluble complexes of one part of the diastereomers are allowed to crystallize out in the presence of lower aliphatic alcohols or aliphatic or cyclic hydrocarbons and are separated off, and, if appropriate, the separated-off complexes are epimerized in a third stage in the presence of a solvent and in the presence of an inorganic or organic base, and are recycled to the first stage of the process.

A process has been found for the purification, from chemical impurities, of cyclopropanecarboxylic acid esters of the formula (I), and the acids on which they are based, which is characterized in that the compounds of the formula (I) are reacted with compounds of the formula (II) in the approximate ratio 1:1 or 2:1 in the presence of lower aliphatic alcohols or aliphatic or cyclic hydrocarbons, in the presence of inorganic or organic bases, and the sparingly soluble complexes produced here are separated off.

Complexes of the formula (III)

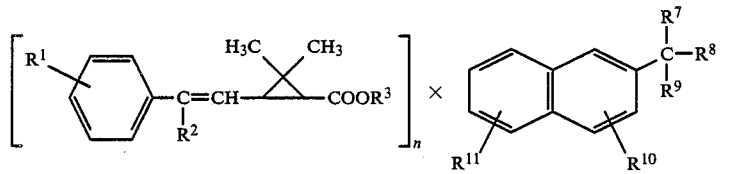

in which $R^1$, $R^2$, $R^3$ and $R^7$ to $R^{11}$ have the abovementioned meaning, and n represents 1 or 2.

Preferably, compounds of the formula (I) are employed in which $R^1$ represents hydrogen or chlorine, $R^2$ represents chlorine, and $R^3$ represents the radical of the formula (a), in which $R^4$ represents hydrogen or CN, $R^5$ represents hydrogen or fluorine, and $R^6$ represents hydrogen.

Flumethrin of the formula

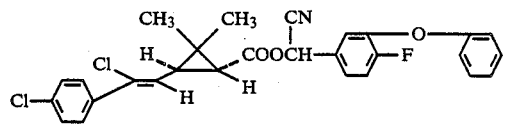

is particularly preferably employed. Flumethrin exists here particularly preferably as a mixture of its train Z isomers (Z refers to the position of the substituents on the vinyl double bond; trans refers to the position of the substituents on the C atoms C1 and C3 of the cyclopropanecarboxylic acid ring).

Compounds of the formula (II) in which $R^7$, $R^8$ and $R^9$ represent hydrogen or, together with the C atom to which they are bound and with the adjacent C atoms form a fused benzene ring, $R^{10}$ represents hydrogen or methyl, and $R^{11}$ represents hydrogen or methyl are preferably employed.

The following may be mentioned in particular: 2-methylnaphthalene, 2,6-dimethylnaphthalene, 2,3-dimethylnaphthalene, anthracene and phenanthrene.

The following may preferably be mentioned as lower aliphatic alcohols: methanol, ethanol, propanols, and butanols. Isopropanol may be mentioned in particular.

Hexane and cyclohexane may be mentioned as lower aliphatic or cyclic hydrocarbons, and cyclohexane may be mentioned particularly.

The complex formation may be carried out in a simple fashion by reacting 1 mol of compounds of the formula (I) with 1 or 0.5 mol of compounds of the formula (II) between 0° to 50° C., if appropriate in the presence of a solvent. The abovementioned lower aliphatic alcohols or hydrocarbons are preferably employed as solvent.

Industrially prepared flumethrin comprises a mixture of the trans Z isomers 1R 3S αR and 1S 3R αS and 1R 3S αS and 1S 3R αR.

In industrially prepared flumethrin, the pairs of enantiomers are present, for example, in the following ratio: 1R 3S αR and 1S 3R αS=60%, 1R 3S αS and 1S 3R αR=40%.

The process can also be used for the industrial purification of, for example, industrially prepared flumethrin (trans Z isomers). On an industrial scale, flumethrin can be purified by distillation or recrystallization only with great difficulty. The process according to the invention allows industrially prepared flumethrin containing chemical impurities to be purified in a simple fashion. Industrial flumethrin (trans Z isomers) is dissolved in isopropanol, and compounds of the formula (IV) are added in the presence of inorganic or organic bases. Sparingly soluble complexes of the isomers 1R 3S R and 1S 3R S are produced in this fashion. These are separated off and may be used as such or, after dissolution in a suitable solvent, epimerized in the presence of inorganic or organic bases to form the isomers 1R 3S R, 1S 3R S, 1R 3S S and 1S 3R R. This mixture can subsequently be isolated or, if appropriate, recycled to the separation described above.

Suitable bases are alkali metal and alkalineearth metal hydroxides, carbonates and bicarbonates, ammonia, and primary, secondary and tertiary amines, such as methylamine, dimethylamine, isopropylamine, diisopropylamine, triethylamine, trimethylamine, pyridine and di-s-butylamine.

The complexes of the formula (III) produced in the new process are to be mentioned particularly. In the case of flumethrin, the following complexes may preferably be mentioned here: (flumethrin trans Z 1R-3S-αR and 1S-3R-αS)$_2$×2,6-dimethylnaphthalene and (flumethrin trans Z 1R-3S-αR and 1S-3R-αS)$_2$×anthracene (flumethrin trans Z 1R-3S-αR and 1S-3R-αS)$_2$×phenanthrene (flumethrin trans Z 1R-3S-αR and 1S-3R-αS)$_2$×2,3-dimethylnaphthalene (Flumethrn 1R-3S-αR and 1S-3R-αS)$_2$×2-methyl-naphthalene.

They are prepared in the process described above. They can easily be cleaved by dissolving in an organic solvent, such as, for example, toluene or chloroform. However, they can also be used as such in insecticidal and ectoparasiticidal agents or for the preparation of such agents.

The less active isomers from the mixture of isomers of industrially prepared flumethrin can be separated off with the aid of the trans Z 1R 3S αR and 1S 3R αS complexes of flumethrin described. The trans Z pair of enantiomers 1R 3S αS and 1S 3R αR are thus obtained in the residue essentially free of the pair of enantiomers trans Z 1R 3S αR and 1S 3S αS (<20%).

The pair of enantiomers trans Z 1R 3S αS and 1S 3R αR is new and is particularly suitable for combating ectoparasites.

Example A

Test with Stomoxys calcitrans
Solvent:
35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the particular desired concentration.

10 adult Stomoxys calcitrans are placed in Petri dishes containing filter papaer discs of appropriate size which have been saturated one day before the start of the experiment with 1 ml of the active compound preparation to be tested. After 3 hours, the degree of destruction is determined.

In this test, the mixture from Example 3 exhibits a 100% action at a concentration of 100 ppm.

Example B

Test with Musca autumnal is
Solvent:
35 parts by weight of ethylene glycol monomethyl ether
35 parts by weight of nonlyphenol polyglycol ether To produce a suitable preparation of active compound, three parts by weight of active compound are mixed with seven parts by weight of the solvent mixture indicated above, and the concentrate thus obtained is diluted with water to the particular desired concentration.

10 adult Musca autumnalis are placed in Petri dishes containing filter paper discs of appropriate size which have been saturated one day before the start of the experiment with 1 ml of the active compound preparation to be tested. After 3 hours, the degree of destruction is determined.

In this test, the mixture from Example 2 exhibits a 100% action at a concentration of 100 ppm.

Example C

Test with Lucilia cuprina res. Larvae
Solvent:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 Lucilia cuprina res. Larvae are introduced into a test tube which contains approx. 1 $cm^2$ of horse muscle and 0.5 ml of the preparation of active compound. After 24 hours, the degree of destruction is determined.

In this test, the mixture from Example 3 exhibits a 100% action at a concentration of 100 ppm.

Example D

Test with Boophilus microplus resistant
Solvent:
35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the particular desired concentration.

10 adult Boophilus microplus res. are immersed for 1 minute in the active compound preparation to be tested. After transfer to plastic beakers and storage in a climatically controlled chamber, the degree of destruction is determined.

In this test, the mixture from Example 3 exhibits a 100% action at a concentration of 100 ppm.

Example 1

0.51 g (1 mmol) of the pair of isomers Z-trans 1R 3S αR and Z-trans 1S 3R αS of flumethrin and 0.078 g (0.5 mmol) of 2,6-dimethlnaphthalene are dissolved in 6 ml of isopropanol with warming to 50° C. After cooling to room temperature, a complex comprising 2 parts of the pair of isomers and 1 part of 2,6-dimethylnaphthalene crystallizes out. After filtering off under suction and drying, 0.55 g are obtained as colorless needles having a melting point of 108° to 109° C.

The following complexes are obtained with the pair of isomers in analogous fashion:

| Complex from A | B | Molar ratio A:B | m.p. |
|---|---|---|---|
| Cl-phenyl-C(Cl)=C(H)-cyclopropyl(CH₃)₂-COO-CH(CN)-phenyl-O-phenyl-F<br>trans-Z—1R—3S—αR<br>trans-Z—1S—3R—αS | 2-methylnaphthalene | 2:1 | 74° C. |
| " | 2,3-dimethylnaphthalene | 2:1 | 90° C. |

| Complex from | | Molar ratio | |
| --- | --- | --- | --- |
| A | B | A:B | m.p. |
| " | 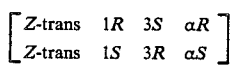 | 2:1 | 124° C. (decomposition) |
| " | 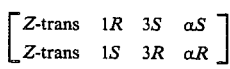 | 2:1 | 78° C. |

Example 2

102 g (0.2 mol) of industrial flumethrin and 9.42 g (0.06 mol) of 2,6-dimethylnaphthalene are dissolved in 1,000 ml of isopropanol with warming to 50° C. The mixture is subsequently allowed to cool slowly to room temperature with stirring. Crystallization slowly commences during this, and can be accelerated by the addition of some of the crystals described in Example 1. For complete crystallization, the mixture is stirred at room temperature for a further 24 hours. The crystals are subsequently filtered off under suction, washed with a little isopropanol, and dried in air. 67 g of a crystalline complex having a melting point of 92° to 98° C. and the following composition are obtained: 2 parts of the pair of isomers I $$\begin{bmatrix} Z\text{-trans} & 1R & 3S & \alpha R \\ Z\text{-trans} & 1S & 3R & \alpha S \end{bmatrix}$$

and +1 part of 2,6-dimethylnaphthalene (=80%) 2 parts of the pair of isomers II $$\begin{bmatrix} Z\text{-trans} & 1R & 3S & \alpha S \\ Z\text{-trans} & 1S & 3R & \alpha R \end{bmatrix}$$

and +1 part of 2,6-dimethylnaphthalene (=20%)

Example 3

The filtrate from Example 2 is freed of solvent in vacuo. The residue is dissolved in toluene and stirred with 30 g of silica gel. The silica gel is subsquently filtered off, and the filtrate is freed of solvent in vacuo. 44 g of a viscous oil having the following distribution of isomers are obtained:
Pair of isomers I
Z-trans 1R 3S $\alpha$R and Z-trans 1S 3R $\alpha$S = 16%
Pair of isomers II
Z-trans 1R 3S $\alpha$S and Z-trans 1S 3R $\alpha$R = 84%

Example 4

67 g of the crystalline complex obtained in Example 2, having a distribution of isomers of pair of isomers I=80% and pair of isomers II=20%, are dissolved in 900 ml of isopropanol with warming to 70° C., and 10 g of triethylamine are then added. The mixture is heated at 70° to 75° C. for 12 hours. It is important here to have a clear solution. The solvent is subsequently removed by distillation in vacuo, and the residue is taken up in 150 ml of toluene and shaken with 100 ml of dilute aqueous hydrochloric acid. The organic phase is separated off and dried, and the toluene is removed by distillation in vacuo. The oil remaining, =66 g, has an isomer composition of pair of isomers I=65%, pair of isomers II=45%. In a further batch, triethylamine was removed by distillation together with approximately ⅓ of the amount of isopropanol. In a further batch, triethylamine was removed by blowing in HCL gas.

Example 5

51 g (0.1 mol) of technical grade flumethrin (~86 % strength) are dissolved with heating to 50° C. in 500 ml of isopropanol and 16 g (0.1 mol) of 2,6-dimethyl-naphthalene and 25 ml triethylamine are added. Under stirring it is cooled to room temperature, slow crystallization commencing. The crystallization can be accelerated by adding a few crystals from Example 1. The mixture is stirred for 48 hours at room temperature. The crystals are subsequently filtered off under suction and dried in air. 50 g of a crystalline complex having a melting point of 88° to 92° C. and the following composition are obtained: 2 parts of the pair of isomers I+1 part of 2,6-dimethyl-naphthalene (=80%) 2 parts of the pair of isomers II+1 part of 2,6-dimethyl-naphthalene (=20%)

The crystalline complex is then epimerized with triethylamine as described in Example 4. A substance having a ratio of isomers of pair of isomers I=55% pair of isomers II=45% and a content of the pair of isomers I and the pair of isomers II=94% is thus again obtained.

Example 6

2.85 g 0.01 mol) of (±) trans-Z-3-[2-chloro-2-(4-chlorophenyl)vinyl]-2,2-dimethylcyclopropane-1-carboxylic acid and 1.56 g (0.01 mol) of 2,3-dimethylnaphthalene are dissolved in 50 ml of isopropanol with warming to 50° C. The mixture is subsequently cooled to room temperature and stirred for a further 10 hours at room temperature. The crystals which precipitate out are filtered off under suction. 1.4 g of a complex comprising 2 parts of (±)-trans-Z-3-[2-chloro-2-(4-chlorophenyl)vinyl]-2,2-dimethyl-cyclopropanecarboxylic acid and 1 part of 2,3-dimethylnaphthalene are obtained as colorless crystals having a melting point of 128° to 132° C.

Example 7

The following complex is obtained analogously to Example 6:

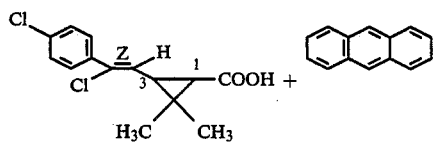

2 parts $\left\{\begin{array}{c}\text{Z-trans-1R-3S}\\\text{Z-trans-1S-3R}\end{array}\right\}$ + 1 part Melting point of the complex 160° C. (decomposition)

It will be understood that the specification and examples are illustrative but not limitative of the present invention and that other embodiments within the spirit and scope of the invention will suggest themselves to those skilled in the art.

We claim:

1. A process for the separation of mutually diastereomeric forms of a cyclopropanecarboxylic acid ester of the formula

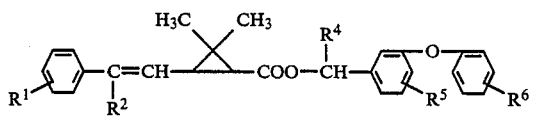

in which
   $R^1$ is selected from the group consisting of hydrogen and halogen,
   $R^2$ is selected from the group consisting of hydrogen and halogen.
   $R^4$ is selected from the group consisting of hydrogen, CN, —C≡CH and $CH_3$,
   $R^5$ is selected from the group consisting of hydrogen and halogen, and
   $R^6$ is selected from the group consisting of hydrogen and halogen,
comprising reacting such ester in a first stage with a second compound in a molar ratio of ester to second compound selected from the group consisting of 2:1 and 1:1, the second compound having the formula

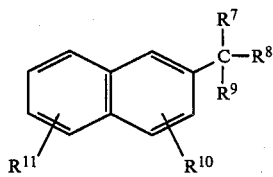

in which
   $R^7$, $R^8$ and $R^9$ each is selected from the group consisting of hydrogen and methyl, or, together with the C atom to which they are bound and with an adjacent C atom of the $R^{10}$-carrying ring form a fused 6-membered ring,
   $R^{10}$ is selected from the group consisting of hydrogen, methyl, ethyl, halogen, amino, methylamino, and
   $R^{11}$ is selected from the group consisting of hydrogen, methyl and ethyl to form complexes, and,
in a second stage allowing the less soluble complexes of one part of the diastereomers to crystallize out in the presence of a solvent selected from the group consisting of a lower aliphatic alcohol, an aliphatic hydrocarbon and a cyclic hydrocarbon, and separating off the crystallized complex from the still dissolved material.

2. A process according to claim 1, in which the ester is flumethrin.

3. A process according to claim 1, in which
   $R^7$, $R^8$ and $R^9$ each is selected from the group consisting of hydrogen, or together with the C atom to which they are bound and with the adjacent C atoms form a fused benzene ring,
   $R^{10}$ is selected from the group consisting of hydrogen and methyl, and
   $R^{11}$ is selected from the group consisting of hydrogen and methyl.

4. A process according to claim 1, in which the second compound is 2-methylnaphthalene, 2,6-dimethylnaphthalene, 2,3-dimethylnaphthalene, anthracene or phenanthrene.

5. A process according to claim 1, wherein the solvent is methanol, ethanol, a propanol, a butanol, hexane or cyclohexane.

6. A process according to claim 1, wherein the solvent is isopropanol or cyclohexane.

7. A process according to claim 1, wherein the first and second stages are effected simultaneously.

8. A process according to claim 1, including the further steps of epimerizing the separated off complex in the presence of a solvent and of a base, and recycling the epimerized material to the first step.

9. A process for the purification, from chemical impurities, of a cyclopropanecarboxylic acid or ester of the formula

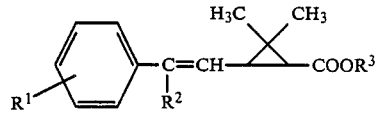

in which
   $R^1$ is selected from the group consisting of hydrogen and halogen,
   $R^2$ is selected from the group consisting of hydrogen and halogen,
   $R^3$ is selected from the group consisting of hydrogen or

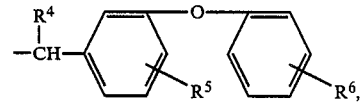

$R^4$ is selected from the group consisting of hydrogen, CN, —C≡CH and $CH_3$,
   $R^5$ is selected from the group consisting of hydrogen and halogen, and
   $R^6$ is selected from the group consisting of hydrogen and halogen,
comprising reacting the ester with about half or an equal molar amount of a second compound of the formula

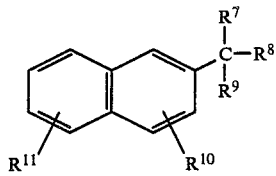

in which
R[7], R[8] and R[9] each is selected from the group consisting of hydrogen and methyl, or, together with the C atom to which they are bound and with an adjacent C atom of the R[10]-carrying ring form a fused 6-membered ring,
R[10] is selected from the group consisting of hydrogen, methyl, ethyl, halogen, amino, methlamino and dimethylamino, and
R[11] is selected from the group consisting of hydrogen, methyl and ethyl,
in the presence of a lower aliphatic alcohol or aliphatic or cyclic hydrocarbon and in the presence of base, and separating off the resulting sparingly soluble complex.

10. A complex of the formula

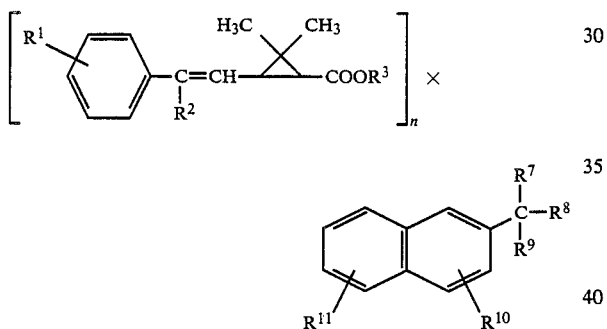

in which
R[1] is selected from the group consisting of hydrogen and halogen,
R[2] is selected from the group consisting of hydrogen and halogen, and
R[3] is selected from the group consisting of hydrogen and

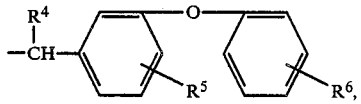

R[4] is selected from the group consisting of hydrogen, CN, —C≡CH and CH[3],
R[5] is selected from the group consisting of hydrogen and halogen and,
R[6] is selected from the group consisting of hydrogen and halogen,
R[7], R[8] and R[9] each is selected from the group consisting of hydrogen and methyl, or, together with the C atom to which they are bound and with an adjacent C atom of the R[10]-carrying ring form a fused 6-membered ring,
R[10] is selected from the group consisting of hydrogen, methyl, ethyl, halogen, amino, methylamino and dimethylamino,
R[11] is selected from the group consisting of hydrogen, methyl and ethyl, and
n is selected from the group consisting of 1 and 2.

11. A complex according to claim 10, in which
R[1] is Cl in para position,
R[2] is Cl, and
R[3] is

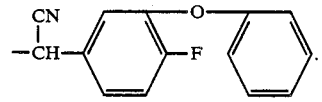

12. A complex according to claim 10, in which

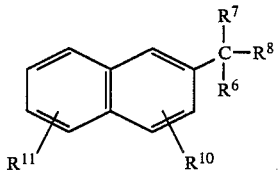

is 2-methylnaphthalene, 2,6-dimethylnaphthalene, 2,3-dimethylnaphthalene, anthracene or phenanthrene.

13. Trans-Z-flumethrin having a content of greater than 80% of the 1R 3S αS and 1S 3R αR pair of enantiomers.

* * * * *